United States Patent [19]
Bonekamp et al.

[11] Patent Number: 5,705,362
[45] Date of Patent: Jan. 6, 1998

[54] MODIFIED SIGNAL SEQUENCES

[75] Inventors: Alfonsus Johannes Bonekamp, Delft; Marcellis Wilhelmus Elisabeth Maria Van Tilborg, Leiden, both of Netherlands

[73] Assignee: Gist-brocades, N.V., Netherlands

[21] Appl. No.: 960,510

[22] Filed: Oct. 13, 1992

[30] Foreign Application Priority Data

May 25, 1992 [EP] European Pat. Off. ............. 92201492

[51] Int. Cl.$^6$ .............. C12N 15/09; C12N 1/21; C12N 15/24; C12N 15/56
[52] U.S. Cl. ............. 435/69.8; 435/69.1; 435/252.31; 435/252.3; 536/23.1; 536/23.4; 536/23.2; 536/23.5; 536/23.7; 530/350; 530/351
[58] Field of Search ................... 530/350, 351; 536/23.7, 23.1, 23.4, 23.5, 23.2; 435/69.1, 69.8, 252.31, 252.3

[56] References Cited

U.S. PATENT DOCUMENTS

| | | | |
|---|---|---|---|
| 4,711,843 | 12/1987 | Chang | 435/69.1 |
| 4,711,844 | 12/1987 | Chang | 435/252.3 |
| 4,769,327 | 9/1988 | Stephens et al. | 435/68 |
| 5,010,000 | 4/1991 | Palva | 435/69.1 |
| 5,013,653 | 5/1991 | Huston et al. | 435/69.7 |
| 5,128,450 | 7/1992 | Urdal et al. | 530/351 |
| 5,141,922 | 8/1992 | Krivi | 514/12 |
| 5,166,322 | 11/1992 | Shaw et al. | 530/351 |

FOREIGN PATENT DOCUMENTS

| | | |
|---|---|---|
| 0196864 | 12/1986 | European Pat. Off. |
| 9010705 | 9/1990 | WIPO |

OTHER PUBLICATIONS von Heijne et al., "Species-specific variation in signal peptide design: Implications for protein secretion in foreign hosts" *FEBS Letters* (1989) 244(2):439–446.

Heikinheimo et al., "Production of pectin methylesterase from *Erwinia chrysanthemi* B374 in *Bacillus subtilis*" *Appl. Microbiol. Biotechnol.* (1991) 35:51–55.

Kalkkinen, N., et al., FEBS Letters, vol. 200, No. 1, pp. 18–22, May, 1986.

Hasegawa, M., et al., European Journal of Biochemistry, vol. 210, No. 1, pp. 9–12, Nov., 1992.

Von Heijne, G., Nucleic Acids Research, vol. 14, No. 11, pp. 4683–4690, Jun., 1986.

Otsuka, T., et al., The Journal of Immunology, vol. 140, No. 7, pp. 2288–2295, Apr., 1988.

Von Heijne et al. (1986) Nuc. Acids. Res. 14(11), 4683–4690.

Nakayama, A., et al., "Efficient secretion of the authentic mature human growth hormone by *Bacillus subtilis*," *Journal of Biotechnology* (1988) 8:123–134.

Yamaguchi, K., et al, "Random Point Mutation Analysis of the Signal Peptide Cleavage Area of *Bacillus stearothermophilus* x–Amylase," *Agric. Biol. Chem.* (1991) 55:11, 2875–2876.

*Primary Examiner*—Rebecca E. Prouty
*Attorney, Agent, or Firm*—Morrison & Foerster LLP

[57] ABSTRACT

The present invention describes a method for reducing processing ambiguity of signal peptidases. Specifically, the C-terminus of a signal sequence is mutated in a such a manner that the secreted protein contains the correct N-terminal amino acid.

Furthermore, the present invention provides an hIL-3 which is essentially homogenous at its N-terminus.

18 Claims, 7 Drawing Sheets

```
                        EcoRI    NdeI
1    5' - GAC.TGC.GAA.TTC.CAT.ATG.TTT.CAC.ATT.GAA.AGG - 3'

2A   5' - GGG.AGC.CGC.|AGA.TGC.AGA|.AGA.ATG.AGG.CAG.CAA.GAA - 3'

2B   5' - GGG.AGC.CGC.|CGC.TGC.ACC|.AGA.ATG.AGG.CAG.CAA.GAA - 3'

2C   5' - GGG.AGC.CGC.|CGC.TGC.TTT|.AGA.ATG.AGG.CAG.CAA.GAA - 3'

2D   5' - GGG.AGC.CGC.|CGC.TGC.GAA|.AGA.ATG.AGG.CAG.CAA.GAA - 3'
                        mutation site 3A   5' - CCT.CAT.TCT.|TCT.GCA.TCT|.GCG.GCT.CCC.ATG.ACC.CAG - 3'

3B   5' - CCT.CAT.TCT.|GGT.GCA.GCG|.GCG.GCT.CCC.ATG.ACC.CAG - 3'

3C   5' - CCT.CAT.TCT.|AAA.GCA.GCG|.GCG.GCT.CCC.ATG.ACC.CAG - 3'

3D   5' - CCT.CAT.TCT.|TTC.GCA.GCG|.GCG.GCT.CCC.ATG.ACC.CAG - 3'
                                    EcoRI
4    5' - CGT.CAG.TTT.CCT.CCG.GAA.TTC - 3'
```

FIG. 3

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Ser Ala Ala Ala Ala
1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

His Ser Ala Ala Ala Ala
1                        5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

His Ser Ala Ala Ala Ala Ala Pro
1                   5

( 2 ) INFORMATION FOR SEQ ID NO:4:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

```
Met Lys Gln Gln Lys Arg Leu Tyr Ala Arg Leu Leu Thr Leu Leu Phe
 1               5                  10                  15
Ala Leu Ile Phe Leu Leu Pro His Ser Ser Ala Ser Ala
            20                  25
```

( 2 ) INFORMATION FOR SEQ ID NO:5:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( x i ) SEQUENCE DESCRIPTION: SEQ ID NO:5:

```
Met Lys Gln Gln Lys Arg Leu Tyr Ala Arg Leu Leu Thr Leu Leu Phe
 1               5                  10                  15
Ala Leu Ile Phe Leu Leu Pro His Ser Gly Ala Ala Ala
            20                  25
```

( 2 ) INFORMATION FOR SEQ ID NO:6:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( x i ) SEQUENCE DESCRIPTION: SEQ ID NO:6:

```
Met Lys Gln Gln Lys Arg Leu Tyr Ala Arg Leu Leu Thr Leu Leu Phe
 1               5                  10                  15
Ala Leu Ile Phe Leu Leu Pro His Ser Lys Ala Ala Ala
            20                  25
```

( 2 ) INFORMATION FOR SEQ ID NO:7:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( x i ) SEQUENCE DESCRIPTION: SEQ ID NO:7:

```
Met Lys Gln Gln Lys Arg Leu Tyr Ala Arg Leu Leu Thr Leu Leu Phe
 1               5                  10                  15
Ala Leu Ile Phe Leu Leu Pro His Ser Phe Ala Ala Ala
            20                  25
```

( 2 ) INFORMATION FOR SEQ ID NO:8:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:8:

```
Ala Ala Ala Ala Ala Pro
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GACTGCGAAT TCCATATGTT TCACATTGAA AGG                  33

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGGAGCCGCA GATGCAGAAG AATGAGGCAG CAAGAA                36

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGGAGCCGCC GCTGCACCAG AATGAGGCAG CAAGAA                36

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGGAGCCGCC GCTGCTTTAG AATGAGGCAG CAAGAA                36

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GGGAGCCGCC GCTGCGAAAG AATGAGGCAG CAAGAA                36

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCTCATTCTT CTGCATCTGC GGCTCCCATG ACCCAG                36

-continued (2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:15:

CCTCATTCTG GTGCAGCGGC GGCTCCCATG ACCCAG     36

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:16:

CCTCATTCTA AAGCAGCGGC GGCTCCCATG ACCCAG     36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

CCTCATTCTT TCGCAGCGGC GGCTCCCATG ACCCAG     36

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

CGTCAGTTTC CTCCGGAATT C     21

MODIFIED SIGNAL SEQUENCES

TECHNICAL FIELD

The present invention relates to the field of genetic engineering. Specifically, the invention relates to the secretion of recombinant proteins by microorganisms.

BACKGROUND OF THE INVENTION

Many secreted and membrane bound proteins are synthesized in a precursor form. This precursor molecule contains a $NH_2$-terminal extension of 15–30 amino acids, the signal or leader peptide. This additional peptide sequence assists the protein in traversing the cell membrane. There is great variability as to the length and the sequence of these peptides. This variability can be observed when the same protein is considered obtained from different species (intraspecies) but also when different proteins are considered from the same species (interspecies).

In spite of the observed variation there are some general structural characteristics which must be satisfied in order for these peptides to be correctly processed and to correctly perform their function in membrane transport. Signal peptides have a basic N-terminal region followed by a central hydrophobic core which is of sufficient length to span the membrane. At the C-terminus there usually is a small uncharged amino acid.

The signal peptides are cleaved by the so-called signal peptidases. It has turned out that these peptidases preferentially recognize certain amino acid sequences, and that this recognition is host specific. For example, the Bacillus signal peptidase I recognizes the sequence Ala-X-Ala, wherein X may be any amino acid, and cleaves the protein downstream of this sequence. Some caution is needed however, since the cleavage specificity also depends on the amino acids following the C-terminus of the signal peptide. Many secretory Bacillus proteins are known and the sites for enzymic digestion have been characterised, Von Heijne and Abrahmsen, FEBS Lett. 244 439–446 (1989).

The use of wild-type (or unmodified) signal sequences for secretion of both heterologous and homologous proteins from Bacilli has been described.

Chang (U.S. Pat. No. 4,711,843) describes the production and secretion of heterologous proteins in *Bacillus subtilis* transformed with vectors containing the gene of interest operably linked with the signal sequence from the β-lactamase gene of *Bacillus licheniformis*.

Palva (U.S. Pat. No. 5,010,000) describes a method for the production and secretion of selected proteins or a part thereof in Bacillus strains by joining the DNA coding for the selected protein to the signal sequence of α-amylase from *Bacillus amyloliquefaciens*.

Stephens et al. (U.S. Pat. No. 4,769,327) describe a vector comprising the secretory signal-encoding sequence of the *Bacillus licheniformis* α-amylase gene and the use of such a vector for the production and secretion of heterologous proteins from Bacilli.

Heikinheimo et al. (Appl.Microbiol.Biotechnol.(1991) 35:51–55) have reported that the use of α-amylase signal sequence of *Bacillus amyloliquefaciens* for the production of heterologous proteins may give rise to a heterogeneous product.

Among the recombinant DNA products, pharmaceutical proteins hold a prominent position. As indicated above, heterogeneous products may be formed depending on the signal sequence which is used. Such products often show increased immunogenicity. In order to avoid such unwanted side-reactions it is important that products should be as homogeneous as possible. This homogeneity is also important from a registrational point of view and is therefore of wider importance than only in the production of pharmaceutical proteins. The unspecific cleavage should therefore be minimized.

The present invention describes a method for minimizing observed heterogeneity. This method is based on the specific modification of the amino acids around the signal peptidase cleavage site.

Modified signal peptides are known for example from Chang (U.S. Pat. No. 4,711,844) who describes modified penicilinase signal peptides and from Chang et al. (EP 196 864) wherein modified pho A signal peptides are described. In general these modified sequences are made to obtain or improve secretion of desired proteins and not to reduce processing ambiguity of otherwise normally secreted proteins.

SUMMARY OF THE INVENTION

The present invention discloses a method for altering the C-terminus of a signal sequence in such a way that cleavage ambiguity is avoided.

Specifically, the present invention discloses a method for reducing signal peptidase cleavage ambiguity in signal peptides having two overlapping cleavage sites. More specifically, the signal peptidase cleavage ambiguity is reduced in signal peptides which contain at least four alanines at their C-terminus. Part of the invention is characterized in that the alanine at position −4 is replaced with a serine, a glycine, a lysine or a phenylalanine residue. It is also possible to reduce the ambiguity by replacing amino acids at position −1, or by deleting an amino acid.

The present invention can also be used to add an extra amino acid to a desired N-terminus. In the case of four Ala's described before this would be possible by altering the amino acids at positions −3 or −1.

The present invention further discloses modified signal sequences which upon cleavage give rise to a homogeneous protein product and wherein the protein contains the correct N-terminus.

The wild type signal sequences are obtained from genes encoding proteins that are normally secreted from Bacilli. Specifically, the present invention provides modified α-amylase signal sequences obtained from *B. licheniformis*.

The present invention further discloses DNA expression products which have a homogeneous N-terminus and a method for obtaining such products.

BRIEF DESCRIPTION OF THE FIGURES

FIG. 3 shows the synthetic probes used to obtain the desired amino acid replacements (SEQ ID Nos:7–16).

DETAILED DESCRIPTION OF THE INVENTION

Figure 1:
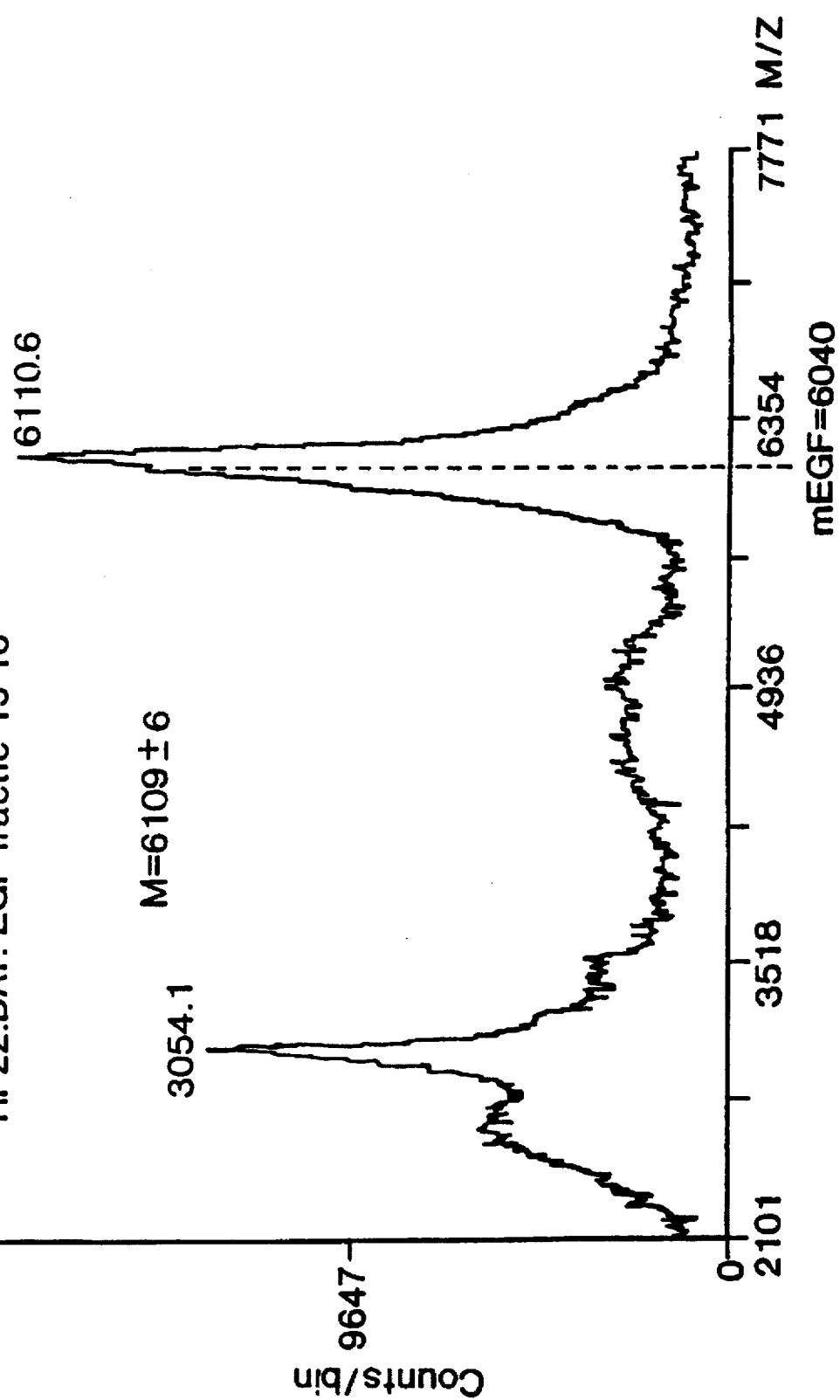
FIG. 1 shows a mass spectrum recorded from collected material of mEGF. MH+ ions are found at m/z 6109+/−6.

The present invention discloses a method for overcoming cleavage ambiguity in the production of recombinant proteins. In the present context cleavage ambiguity is defined as the production of secreted recombinant proteins which are heterogeneous at their N-terminus and wherein said heterogeneity is due to the presence of more than one cleavage site for the signal peptidase of the host cell used. More particularly the cleavage sites overlap in such a way that the –2 site of the first cleavage site corresponds with the –1 site of the second and the –3 of the first with the –2 of the second.

The present inventors found for the first time that the use of the α-amylase signal sequence from *Bacillus licheniformis* resulted in an N-terminally heterogeneous product. Closer inspection of the α-amylase signal sequence from *Bacillus licheniformis* showed that this sequence has the following C-terminal amino acid sequence:

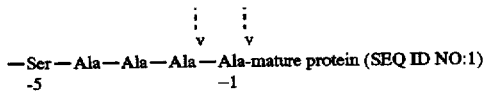

this sequence contains two potential sites for signal peptidase digestion (as indicated with an arrow), provided that the first amino acid of the mature protein does not interfere with the cleavage between amino acids –1 and +1. These cleavage sites may give rise to two different mature proteins having either the correct sequence or one extra amino acid, Ala, at the N-terminus. Thus the use of the α-amylase signal sequence from *B. licheniformis*, for the secretion of heterologous or homologous proteins, may give rise to a heterogeneous product consisting of a mixture of mature protein and protein having an additional amino acid at the N-terminus. This heterogeneity is indicated as processing ambiguity throughout the present specification.

The method proposed for overcoming this ambiguity is applicable for every combination of signal sequence/mature protein. Not every combination however gives rise to this problem, which was detected during the analysis of pharmaceutical proteins produced by Bacillus strains.

In general cleavage ambiguity can be overcome by replacing one signal sequence by another. One could, for example, replace the α-amylase signal sequence from *Bacillus licheniformis* by the one from *Bacillus subtilis* or *Bacillus amyloliquefaciens*.

The present invention focuses on the replacement of amino acids between the –4 and the +1 of the signal sequence. It is an aim of the present invention to obtain proper cleavage and to obtain the mature protein with its natural N-terminal amino acid.

In its basic form the method consists in replacing one or more amino acids at the C-terminus of the signal sequence in such a way that the only possible cleavage site-left is at the desired position. For this to be proper reasoning, it has to be assumed that the cleavage by the signal peptidase as such depends on the combination of the C-terminal amino acids of the signal peptide and the NH₂-terminal amino acids of the mature protein.

Another aim of the invention is the possibility of adding or deleting specific amino acids around cleavage sites, again giving rise to reduction of cleavage ambiguity.

As an example we use the *Bacillus licheniformis* α-amylase signal peptide sequence. This sequence has the following C-terminal sequence:

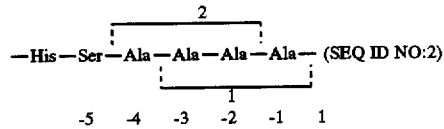

Wherein 1 and 2 indicate the recognition sites of the signal peptidase. Digestion takes place at the right side of the recognition sites.

To obtain a proper mature product, recognition site 2 has to be destroyed without interfering with recognition site 1. This means that the Alanine residues of positions –4 and/or –2 have to be altered. Alternatively, the Ala residue at position –4 may be deleted.

The combination of the *B. licheniformis* α-amylase signal sequence with human IL-3 even shows a third possible cleavage site since mature human IL-3 starts with an Alanine;

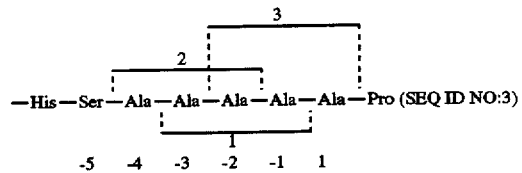

In practice it has turned out that site 3 is not used. Apparently the Bacillus signal peptidase is not active if the Ala-X-Ala is upstream of a Proline.

Comparison of the presented sequence with that of other Bacillus signal sequences suggests some possible alterations which give rise to cleavable signal sequences and at the same time leads to loss of the ambiguity. It is expected that this gives rise to a significant reduction in expression level. *Bacillus stearothermophilus* α-amylase has a Lys at position –4, thereby site 2 is destroyed.

*B. licheniformis* serine protease has a Ser at –4 and at –2 also with these amino acids cleavage site 2 is specifically destroyed.

Another approach for reducing cleavage ambiguity is based on the publications of yon Heijne. Yon Heijne has performed a systematic statistical analysis of the amino acid sequences from both eukaryotic and prokaryotic signal peptides. This analysis led him to propose that an acceptable cleavage site should fulfil what he called the "(–3, –1) rule". This "rule" indicates that the following structural requirements should be met in order to have a suitable signal peptidase cleavage. The cleavage site preferably must have Ala, Ser, Gly, Cys, Thr or Gln at position –1, and it preferably should not have an aromatic (Phe, His, Tyr, Trp) charged (Asp, Glu, Lys, Arg) or large polar (Asn, Gln) amino acid at position –3. Finally, no Pro should be present between –3 and 1.

In the present situation this means that replacement of Ala at –4 by Gly, Lys or Phe is expected to destroy cleavage site 2 without affecting site 1. More generally, it was found that replacements along this suggested line do not always lead to the expected results. Von Heijne has not suggested to use his findings in the present way. As mentioned above, von Heijne merely gives a statistical analysis of signal sequences.

The present invention can be described as a method for reducing signal peptidase cleavage ambiguity in signal peptides which contain two overlapping cleavage sites. The method is characterized in that the signal sequence is mutated in the codons coding for amino acids at positions −4 and/or −2 with respect to the desired cleavage site in such a way that these positions contain a combination of amino acids not occurring at positions −3 and/or −1 of a signal sequence of the parent organism. Alternatively, it may be desirable to add an amino acid to the N-terminus of a protein. This can be done at the same time as the cleavage ambiguity reduction by modifying amino acids at positions −3 and/or −1.

The method disclosed in the present invention is based on the observation that some amino acids are never found at specific sites near a signal peptidase cleavage site and that this phenomenon is species specific. Therefore potential cleavage sites can be destroyed by specific amino acid replacements. Specifically, when two overlapping signal peptidase cleavage sites are found, one tries to find as many signal peptidase cleavage sites as possible from the given organism. Subsequently, the consistent absence of certain amino acids at position −3 and/or −1 in this organism is analyzed. Finally one mutates the DNA encoding the desired signal sequence in such a way that these 'forbidden' amino acids appear at positions −4 and/or −2 with respect to the signal peptidase cleavage site.

The method is generally applicable for every organism. Specifically the method is illustrated for Bacillus.

The present invention discloses mutant signal sequences, derived from a wild type Bacillus signal sequence that contains overlapping signal peptidase cleavage sites, which has been mutated in the codons coding for amino acids at positions −4 and/or −2 with respect to the desired cleavage site in such a way that these positions contain a combination of amino acids not occurring at positions −3 and/or −1 of a signal sequence of the parent organism.

It is to be understood that the suggested amino acid sequence of the signal sequence obtained after the analysis described above can be obtained in different ways. The DNA encoding the modified signal sequence can be obtained synthetically and subsequently be cloned. The DNA can also be obtained by mutagenizing an existing sequence.

The present invention is illustrated by the use of a mutated Bacillus α-amylase sequence. The following sequences have been used in combination with IL-3:

Met—Lys—Gln—Gln—Lys—Arg—Leu—Tyr—Ala—Arg—
Leu—Leu—Thr—Leu—Leu—Phe—Ala—Leu—Ile—Phe—
Leu—Leu—Pro—His—Ser—Ser—Ala—Ser—Ala— (SEQ ID NO:4)

Met—Lys—Gln—Gln—Lys—Arg—Leu—Tyr—Ala—Arg—
Leu—Leu—Thr—Leu—Leu—Phe—Ala—Leu—Ile—Phe—
Leu—Leu—Pro—His—Ser—Gly—Ala—Ala—Ala— (SEQ ID NO:5)

Met—Lys—Gln—Gln—Lys—Arg—Leu—Tyr—Ala—Arg—
Leu—Leu—Thr—Leu—Leu—Phe—Ala—Leu—Ile—Phe—
Leu—Leu—Pro—His—Ser—Lys—Ala—Ala—Ala— (SEQ ID NO:6)

Met—Lys—Gln—Gln—Lys—Arg—Leu—Tyr—Ala—Arg—
Leu—Leu—Thr—Leu—Leu—Phe—Ala—Leu—Ile—Phe—
Leu—Leu—Pro—His—Ser—Phe—Ala—Ala—Ala— (SEQ ID NO:7)

The examples illustrate the feasibility of the described method. The *Bacillus licheniformis* α-amylase signal sequence/IL-3 fusion gives rise to 20% human Interleukin-3 (hIL-3) with an additional Ala. After incorporation of the amino acid replacements suggested above, no extra Ala could be detected.

In all cases mentioned this indicates a clear reduction in processing ambiguity.

A similar result can be obtained for the combination of the *Bacillus licheniformis* α-amylase signal sequence/mouse Epidermal Growth Factor (EGF), where 80% of the mEGF contains an extra N-terminal Ala.

The described method results in a protein having at least 80% correct N-terminus. Preferably 90% of the mature protein molecules contain the mature N-terminus, more preferably the amount of incorrect proteins is only 5%. In a most preferred embodiment, there is no peak present in HPLC experiments corresponding with an N-terminal extension of the mature protein.

Apart from the reduction in processing ambiguity, we found that there was no reduction in the amount of protein produced. Thus there was a significant increase both in relative and absolute terms of the amount of N-terminally homogeneous product.

If a mature protein is too short or if an extra amino acid is desirable at the N-terminus mutations could also be performed at the −3 and/or −1 site. For example in the IL-3 case as illustrated, one obtains 100% mature IL-3 by altering amino acids −4 and/or −2. By altering amino acids −3 and/or −1, one obtains 1-100% IL-3 with an extra N-terminal Ala.

EXAMPLES

Example 1

Cloning, expression, purification and processing ambiguity of murine EGF

DNA encoding murine EGF was synthesized using the phosphoamidite method as described by Beaucape et al. (1981, Tetrahedron lett. 22: 1859–1862). The encoded sequence corresponds with the sequence disclosed by Savage and Cohen (1972, J.Biol.Chem. 247: 7609–7611). This sequence was developed in such a way that a perfect fusion was made possible between the *B. licheniformis* α-amylase signal sequence and the EGF encoding DNA. The EGF sequence was subsequently cloned in the vector pGB/IL-322 described in the EP-A-390252. Specifically, the PstI-HindIII fragment was replaced, thereby effectively replacing the hIL-3 sequence.

The plasmid was transformed to *B. licheniformis* T9 and cells were grown in TSB medium (30 g/l Tryptone Soya Broth, 10 mg/l manganesulphate and 10 μg/ml neomycine) at 37° C.

After harvesting the cells the EGF was purified using the following standard procedure:

acid precipitation, centrifugation, ultrafiltration, ion-exchange chromatograpy and finally RP-HPLC (according to O'Keefe and Sharry, J. Chromatogr. Biomed. Appl. 336 73–85 (1984)).

Mass spectrometric data were collected under standard conditions by use of a BIO ION Plasma Desorption Mass Spectrometer. The sample was emitted on nitrocellulose coated target.

Mass spectrometry indicates that the EGF molecule (expected mass 6040 daltons) is 6109+/−6 which is about 70 daltons too high (see FIG. 1). Therefore, there is one amino acid too many present in this product.

According to HPLC and Edman degradation data, the EGF has, for about 80% of the molecules an undesirable N-terminal Ala extension.

Example 2

Cloning, expression, purification and processing ambiguity of human IL-3

*Bacillus licheniformis* cells (strain T9), containing pGB/IL-341, were grown in TSB medium (30 g/l Tryptone Soya Broth, 10 mg/l manganesulphate and 10 μg/ml neomycine) at 37° C. The vector pGB/IL-341 was described in EP-390252.

The vector pGB/IL-341 is a pUB110 related vector with the expression cassette: α-amylase promoter; α-amylase ss—complete hIL-3 encoding cDNA; 3'noncoding hIL-3; α-amylase terminater.

For the purification of human IL-3, *B.licheniformis* T9 transformants containing pGB/IL-341 were cultured.

Purification of human IL-3

In order to obtain highly purified hIL-3 from *Bacillus licheniformis* T9 (see WO 88/04691), transformants containing the desired plasmids were cultured and the cells were centrifuged. Briefly, the purification contained the following steps
a) hydrophobic interaction chromatography, b) ultra filtration, c) anion exchange chromatography and d) ultra filtration.

Cell free medium from *B. licheniformis* T9 was brought to 1M $(NH_4)_2SO_4$, adjusted to pH 7.0 with NaOH, loaded on a column of Fractogel TSK-butyl 650 C. (5×5 cm) and, equilibrated in 1M $(NH_4)_2SO_4$ in 10 mM Tris-HCL buffer, pH 7.0. 1 mM Phenylmethylsulfonylfluoride (PMSF) was used as a proteinase inhibitor.

Whereas most of the protein was found in the run-through fractions, hIL-3 was adsorbed to the column. After extensive washing of this column with the same buffer, hIL-3 was eluted using a gradient from 1M to 0.1M $(NH_4)_2SO_4$ in 10 mM Tris-HCl, pH 7.0 (600 ml/hr). Detection was at 280 nm.

Ultra filtration in a 300 ml Amicon stirred cell using 3 kd UF filters was used to adjust the hIL-3 fractions to a pH 7.8 and a conductivity of 0.7 mS.

The hIL-3 was then loaded on a column of Q Sepharose Fast-Flow (50×5 cm) which was equilibrated in a Tris buffer with identical pH and conductivity (with a flow of about 300 ml/h). In this purification step, the volume of the concentrated solution with hIL-3 that was loaded was 6–8% of the total column volume. All active forms of hIL-3 were found in the run-through fractions. The major form of hIL-3 was separated from other hIL-3-like smaller proteins that were also positive in western blotting using antihuman IL-3 antibodies. Finally the fractions were desalted using ultra filtration.

Analysis of human Il-3 purified protein

Purified human IL-3 was characterised by peptide mapping in combination with mass spectrometry. After digestion with selected peptidases, the fragments were separated by HPLC and analysed by mass spectrometry. After digestion with Endo Lys-c, not only the expected mass corresponding to the expected fragment from the first ten amino acids was found, but also a second mass 71 daltons higher was found. In order to quantify the percentage of N-terminal heterogeneity the analysis described below was developed.

The content of a vial (5 μg) Endo Lys-C sequencing grade (Boehringer Mannheim Cat. No. 1047 825) was dissolved in 160 μl ammonium bicarbonate buffer pH 8.5. 50 μl of the enzyme solution was added to about 5 nmol of lyophilised hIL-3 and this reaction mixture was incubated at 37° C. for 90 minutes. For fast complete separation of the fragments of interest the following HPLC procedure was used.

The HPLC (Applied Biosystems 130A) was equiped with a RP-18 (Applied Biosystems Cat. No. 0711-0014). The complete digestion mixture was injected in this system and separation was achieved by application of the following linear gradient 10% solvent A, to 40 or 60% solvent B in 45 minutes at a flowrate of 180 μl a minute.

(Solvent A: 1 ml Trifluoracetic acid in one liter water, solvent B: 0.85 ml Trifluoracetic acid in 300 ml water and 700 ml Acetonitrile). All fractions visible at 214 nm were collected and lyophilised for M.S. analysis if required.

Mass spectrometric data were collected under standard conditions by use of a BIO ION Plasma Desorption Mass Spectrometer or a AMD 604 high resolution mass spectrometer using LSIMS as ionisation mode with DTT\DTE as matrix.

The HPLC chromatogram (IL-3) shows two peaks with a ratio of about 80 to 20%. The mass spectra recorded from collected material showed MH+ ions at m/z1088 and m/z1159 respectively. This corresponds with the mass from the expected N-terminal fragment, amino acids 1–10, and this fragment with an extra Ala at the N-terminus. Based on data from other digestion experiments, other possible substitutions or additions of amino acids could be excluded.

Example 3

Ambiguity reduction in the processing of the α-amylase signal sequence/IL-3 fusion This example describes the introduction of alterations in the *B. licheniformis* α-amylase signal sequence with the PCR-technique. The mutated plasmids were brought to expression in *B. licheniformis* and, after purification of the hIL-3 protein, the N-terminus was characterized.

The following alterations in the α-amylase signal sequence were chosen, refering to the detailed description of the invention.

| position: | −4<br>Ala | −3<br>Ala | −2<br>Ala | −1<br>Ala | +1<br>Ala | +2<br>Pro | (SEQ ID NO: 8) |
|---|---|---|---|---|---|---|---|
| A. | Ser | | Ser | | | | |
| B. | Gly | | | | | | |
| C. | Lys | | | | | | |
| D. | Phe | | | | | | |

Figure 2:
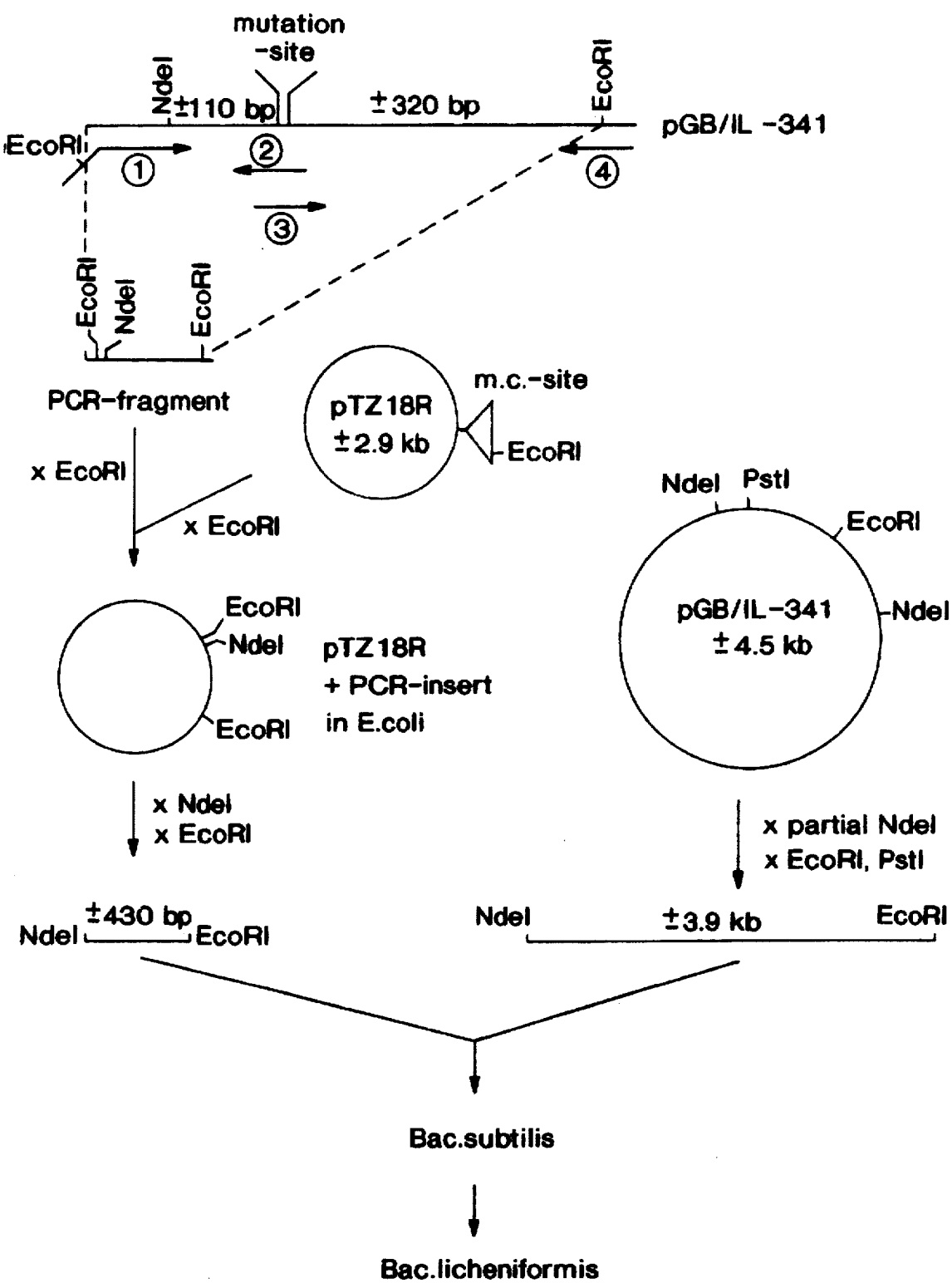
FIG. 2 shows the cloning strategy of hIL-3.
Figure 4:
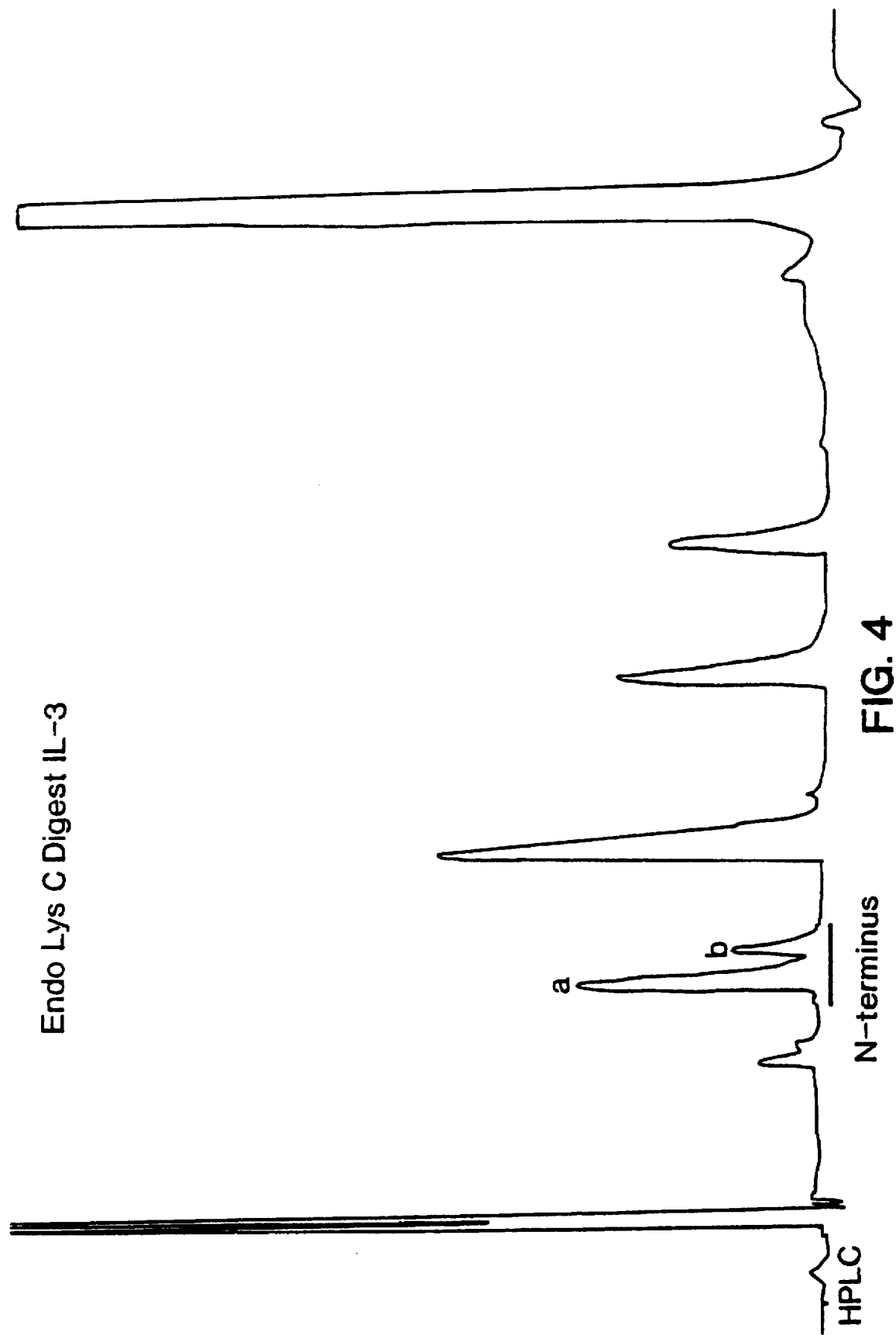
FIG. 4 shows an HPLC chromatogram of complete hIL-3 digested with Endo Lys-C. Peaks A and B are present in a ratio of about 80 to 20%.
Figure 5:
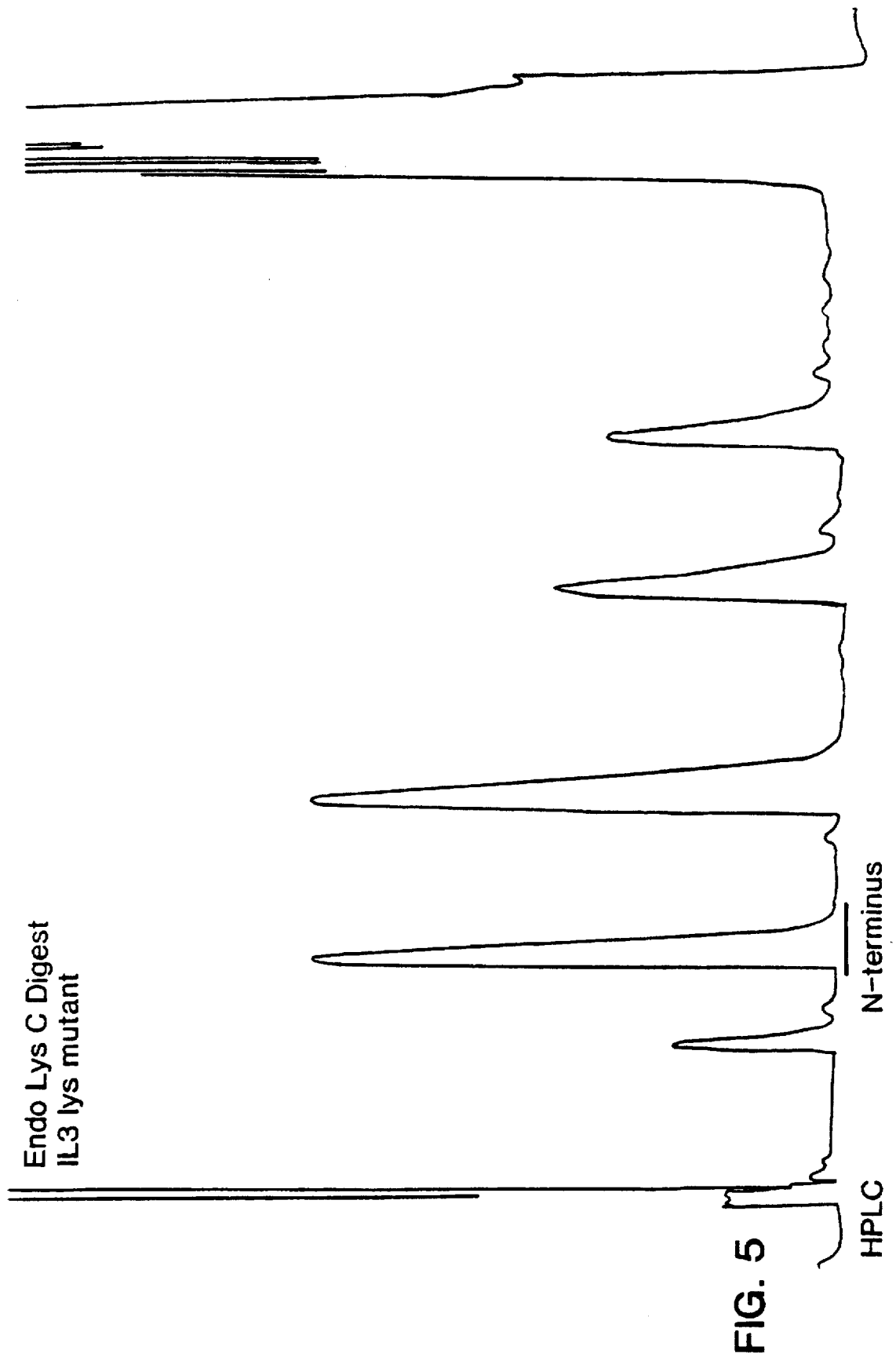
FIG. 5 shows an HPLC chromatogram of the complete hIL-3 digested with Endo-Lys-C after Ala Phe substitution. Peak B is absent.
Figure 6:
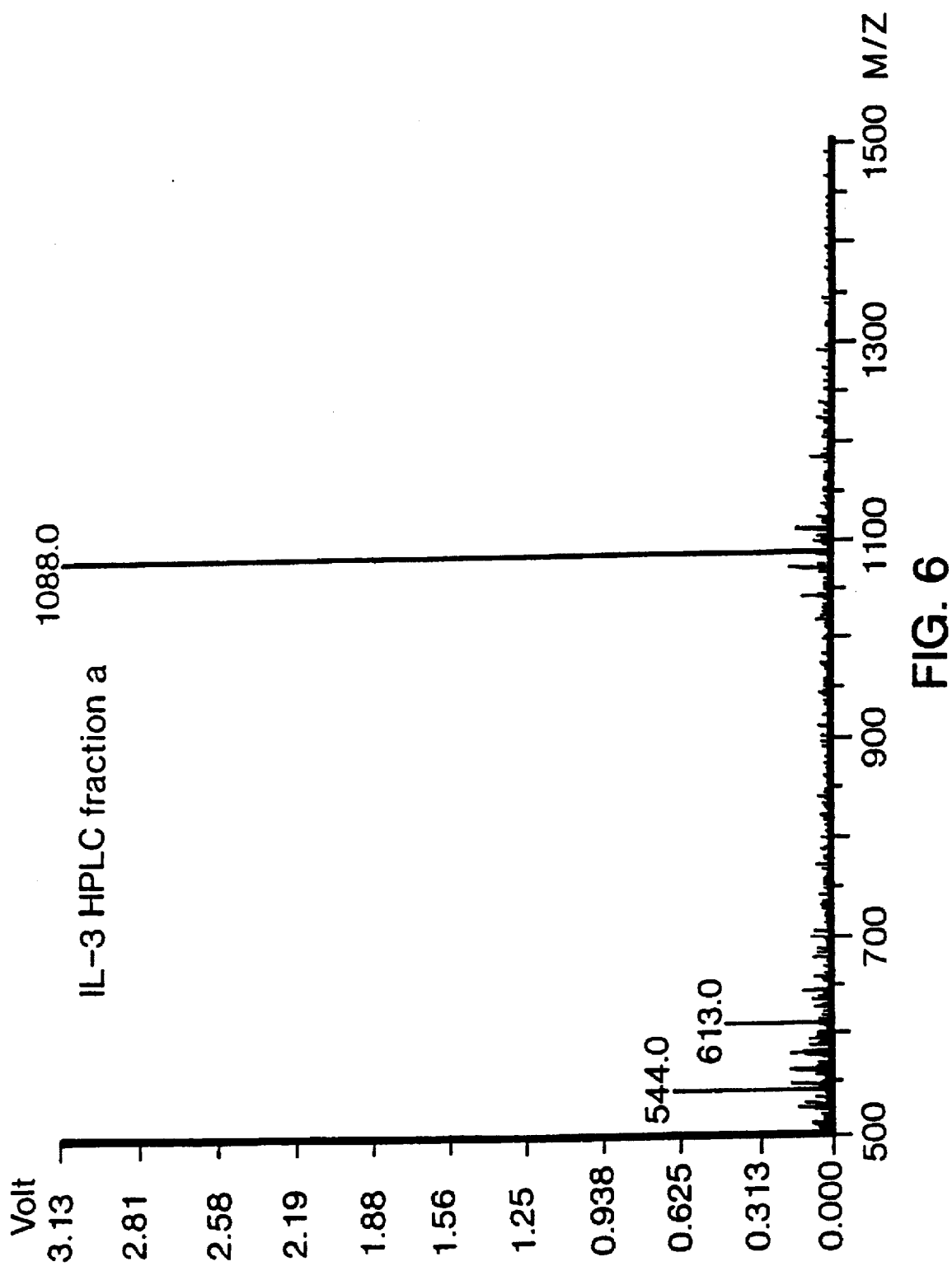
FIG. 6 shows a mass spectrum recorded from collected material of peak A of FIG. 4 MH+ ions are found at m/z1088.
Figure 7:
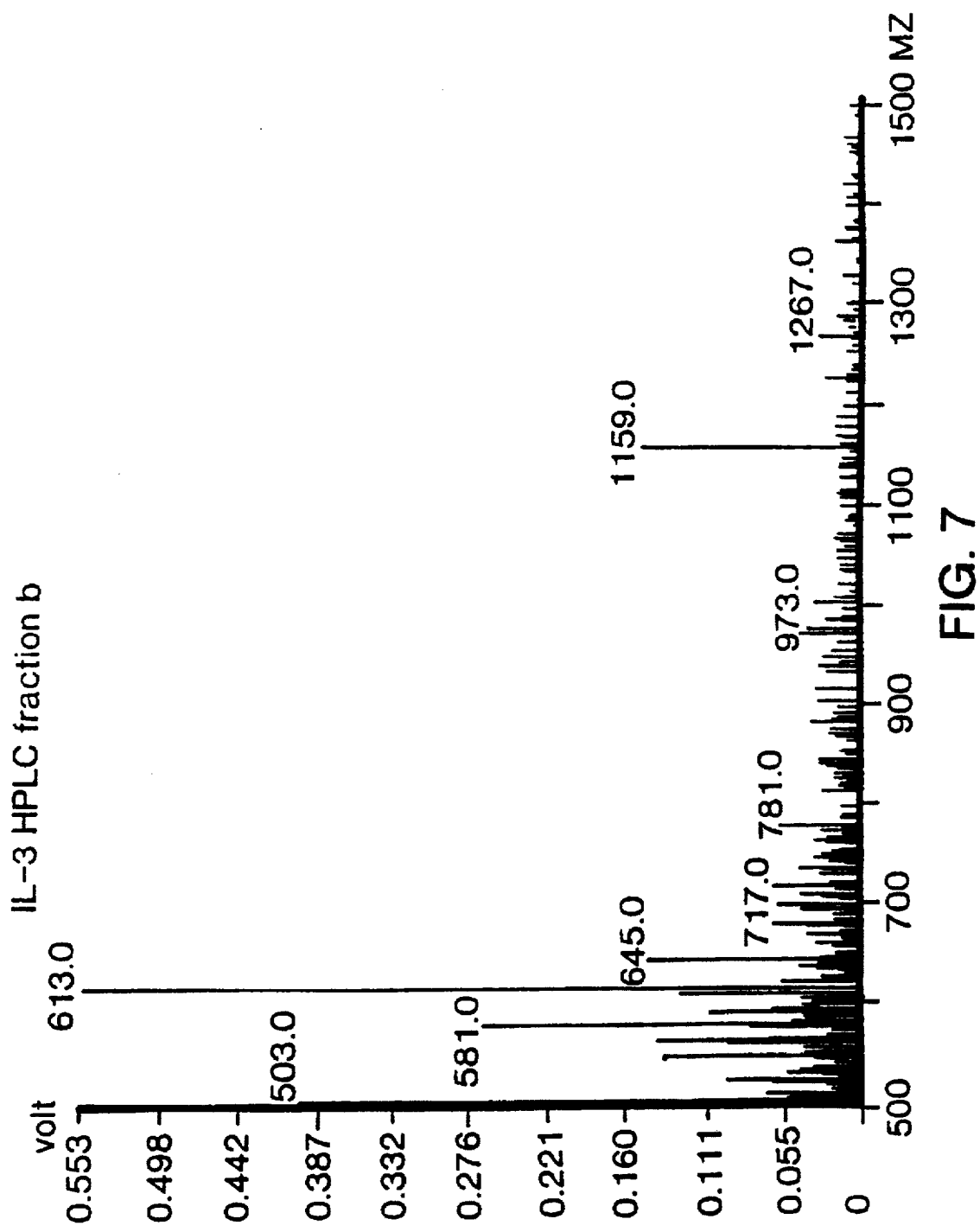
FIG. 7 shows a mass spectrum recorded from collected material of peak B of FIG. 4 MH+ ions are found at m/z1159.

These alterations were introduced with help of PCR. Oligo's were designed with the desired mutations (FIG. 3). Two separate PCR's with oligo's 1 and 2 on the one hand and 3 and 4 on the other hand and a fusion PCR with the products were performed for each mutation A/D (see FIG. 2). The PCR's were done on a Perkin Elmer PCR thermal cycle, procedure see batch analysis AmpliTaq DNA polymerase (Perkin Elmer Cetus). The amount of $MgCl_2$ used was 2 mM; the vector pGB/IL-341: 10 ng, oligo 1 and 4: 0.5 μg and oligo 2 and 3: 50 ng.

The fusion PCR is performed with 100 ng of both PCR fragments and 0.5 μg oligo's. Run: 25 cycli; 2' 94° C., 2' 55° C., 3' 72° C. The PCR fusion fragments were cloned in the EcoRI site of the pTZ18R vector. The plasmids were transformed to *E.coli* JM109 using the $CaCl_2$-method to prepare the competent cells (Sambrook et al, p.1.82 (1989)). The transformants were plated on X-gal and IPTG containing LB-agar plates for blue/white screening. Plasmid DNA was isolated from white colonies by alkaline lysis (Sambrook et al, p.1.25–1.28 (1989)) and analysed on agarose gels after digestion with several restriction enzymes. The pTZ18R-PCR plasmids were sequenced for the absence of PCR-mismatches with the sequenase(R) DNA sequencing kit (USB Corporation).

To exchange the wild type α-amylase signal sequence for a mutated one, the pGB/IL-341 plasmid was digested partial with NdeI and with EcoRI. To isolate the right DNA fragment, the DNA was also digested with PstI. After separating on gel the 3.9 kb NdeI-EcoRI DNA fragment was excised and isolated by electro-elution. The pTZ18R-PCR plasmids were digested with EcoRI and NdeI and the DNA fragments were separated on a 0.7% agarose gel. The PCR-band of 430 bp was isolated from the gel with the Mermaid kit (BIO 101). The PCR band was ligated into the 3.9 kb vector fragment and transformed to *B.subtilis*.

The transformation of *B.subtilis* was performed essentially as described by Niaudet and Ehrlich (1979, Plasmid 2 48–58).

A single colony of a minimal medium agarplate with *B.subtilis* cells (strain 1A40) was transferred to 10 ml 2× Spizizen$^+$ medium (2× Spizizen: 160 mM K$_2$HPO$_4$; 88 mM KH$_2$PO$_4$; 30 mM (NH$_4$)$_2$SO$_4$; 7 mM MgSO$_4$; pH 7.0–7.4, 2× Spizizen$^+$: 2× Spizizen with 0.5% glucose; 0.02% casaminoacids; 50 µg/ml tryptophan; 20 µg/ml methionine; 20 µg/ml lysine) in a 500 ml conical flask. The cells were grown overnight at 37° C. in a gently shaking waterbath. The next morning the culture was diluted until an OD$_{600}$≈0.1 and incubated at 37° C. and 250–300 rpm. The culture was grown for 5–6 hours until OD$_{600}$≈1.0–1.1 and diluted 1:1 with 2× Spizizen medium. The cells were competent after another incubation for 90 min. at 37° C. and 250–300 rpm. In a tube sold under the trade name Universal, 1 ml competent cells and 1 µg DNA were incubated for 1 hour at 37° C. and 250–300 rpm. The cells were plated on minimal agar plates with 10 µg/ml neomycin and incubated at 37° C. After 48–72 hours, the transformants appeared.

Plasmid DNA was isolated from the transformants by alkaline lysis (Sambrook et al, p.1.25–1.28 (1989), the cell pellets were resuspended in lysis buffer with lysozyme (final conc. 2 mg/ml) and incubated for 5 min. at 37° C., before the NaOH/SDS was added. The plasmids were analysed on their size, on gel, after digestion with several restriction enzymes. The plasmids with the mutated signal sequence were transformed to *B.licheniformis* by protoplasts.

The transformation of *B.licheniformis* is described in EP 134048.

Plasmid DNA was isolated from the *B.licheniformis* transformants with the same procedure used for *B.subtilis*, the alkaline lysis. The mutations of the α-amylase signal sequence were analyzed by sequence analysis. The mutants were cultured overnight in TSB-medium with 10 µg/ml neomycin at 37° C. Supernatant was put on a SDS-PAGE gel and blotted to nitrocellulose (Sambrook et al, Molecular Cloning; a laboratory manual (second edition), Cold Spring Harbor Laboratory Press. p.18.47–18.75 (1989)) to determine by immunological detection, the size and the amount of the hIL-3. The productivity of all mutants seems to be at a "normal" level for these cultures in shake flasks, and the size of the hIL-3 does not differ from the transformant with the wild type α-amylase signal sequence.

---

We claim:

1. A nucleic acid molecule that comprises a nucleotide sequence encoding a fusion protein of the formula signal peptide-mature protein wherein said signal peptide has an amino acid sequence modified from that of a corresponding wild-type signal peptide which contains Ala at positions −1 to −4 so that the codon at position −4 has been modified to encode Ser or Gly whereby a signal peptidase cleavage site is removed by said modification.

2. The nucleic acid molecule of claim 1 wherein the codon at position −2 has been modified to encode Ser.

3. The nucleic acid molecule of claim 1 wherein said modification is solely at position −4 of said signal peptide.

4. The nucleic acid molecule of claim 2 wherein the sequence at positions −4 to −1 of the signal peptide is selected from the group consisting of:

Ser-Ala-Ser-Ala; and Gly-Ala-Ala-Ala.

5. The nucleic acid molecule of claim 1 which further comprises control sequences operably linked to said encoding nucleotide sequence capable of effecting its expression.

6. The nucleic acid molecule of claim 1 wherein the codon at position −4 has been modified to encode Ser.

7. A recombinant host cell comprising an expression system for a nucleotide sequence encoding a precursor protein of the formula:

signal peptide-mature protein wherein the signal peptide-encoding nucleotide sequence has been modified from a wild-type signal peptide which contains Ala at positions −1 to −4 so that the codon at position −4 has been modified to encode Ser or Gly so as to reduce amino terminal heterogeneity in said mature protein produced and secreted by said cells.

8. The cell of claim 7 wherein said signal peptide is the α-amylase signal peptide of a Bacillus.

9. The cell of claim 7 wherein the codon at position −2 of said signal peptide has been modified to encode Ser.

10. The cell of claim 7 wherein the codons of said nucleotide sequence at positions −4 to −1 of the modified signal peptide encode an amino acid sequence selected from the group consisting of:

Ser-Ala-Ser-Ala; Gly-Ala-Ala-Ala; and Ser-Ala-Ala-Ala.

11. The cell of claim 7 wherein said codon at position −4 has been modified to encode Ser.

12. The cell of claim 7 wherein said modification is solely at position −4 of said signal peptide.

13. A method to produce a mature protein homogeneous at the N-terminus which method comprises culturing the cells of claim 7 under conditions wherein said nucleotide sequence is expressed and said mature protein is secreted; and recovering the mature protein from the culture medium.

14. The method of claim 13 wherein said mature protein is human IL-3.

15. The method of claim 13 wherein the codon at position −2 of said signal peptide has been modified to encode Ser.

16. The method of claim 13 wherein the codons of said nucleotide sequence at positions −4 to −1 of the modified signal peptide encode an amino acid sequence selected from the group consisting of:

Ser-Ala-Ala-Ala; Gly-Ala-Ala-Ala; and Ser-Ala-Ser-Ala.

17. The method of claim 13 wherein the modification of said signal peptide is solely at the position −4 of said signal peptide.

18. The method of claim 13 wherein said codon at position −4 has been modified to encode Ser.

* * * * *